United States Patent [19]

Westfall et al.

[11] Patent Number: 5,331,995
[45] Date of Patent: Jul. 26, 1994

[54] FLOW CONTROL SYSTEM FOR MEDICAL VENTILATOR

[75] Inventors: Thomas P. Westfall, Riverside; Alberto Ruiz-Vela, Alta Loma; Anthony J. Caterina, Riverside; Clyde R. Visser, Upland, all of Calif.

[73] Assignee: Bear Medical Systems, Inc., Riverside, Calif.

[21] Appl. No.: 916,344

[22] Filed: Jul. 17, 1992

[51] Int. Cl.$^5$ .............................................. G05D 7/06
[52] U.S. Cl. ..................................... 137/8; 128/204.21; 137/468; 137/487; 137/487.5
[58] Field of Search ............... 128/204.21; 137/8, 487, 137/487.5, 468

[56] References Cited

U.S. PATENT DOCUMENTS

| | | | |
|---|---|---|---|
| Re. 29,383 | 9/1977 | Gallatin et al. | 137/14 |
| 2,609,831 | 9/1952 | MacGeorge | 137/487 |
| 3,055,389 | 9/1962 | Brunner | 137/487 |
| 3,923,056 | 12/1975 | Bingmann et al. | |
| 3,961,627 | 6/1976 | Ernst et al. | |
| 3,972,327 | 8/1976 | Ernst et al. | |
| 4,026,321 | 5/1977 | Kahoe et al. | 137/487 |
| 4,277,832 | 7/1981 | Wong | 364/510 |
| 4,344,144 | 8/1982 | Damico et al. | 364/510 |
| 4,527,557 | 7/1985 | DeVries et al. | 128/204.23 |
| 4,602,653 | 7/1986 | Ruiz-Vela et al. | 137/88 |
| 4,637,851 | 1/1987 | Rusz | 128/204.21 |
| 4,796,511 | 1/1989 | Ginn et al. | 137/8 |
| 4,883,051 | 11/1989 | Westenskow et al. | 128/204.21 |
| 4,928,684 | 5/1990 | Breitenfelder et al. | 128/204.21 |
| 4,970,941 | 11/1990 | Reinhardt | 137/625.64 X |
| 5,072,729 | 12/1991 | DeVries | 128/204.23 |
| 5,094,235 | 3/1992 | Westenskow et al. | 128/204.22 |

Primary Examiner—Gerald A. Michalsky
Attorney, Agent, or Firm—Klein & Szekeres

[57] ABSTRACT

A system including the method employed, for controlling the flow of a pressurized gas through a variable orifice flow control valve in a pressurized gas conduit system, such as a ventilator, in response to either a desired flow rate/volume input signal, a desired pressure signal or both. With respect to the flow rate input signal, the system generates a flow signal indicative of the actual flow rate of gas through the flow control valve by measuring the pressure drop across the valve and using the actual orifice area based on a control valve position signal given to the valve. This flow signal is compared to the flow rate input signal to give a correction signal which is used to form a volume flow reference signal. With respect to the desired pressure signal, a signal indicative of the effective pressure at a set location in the system is compared to the desired pressure signal and processed to give a pressure flow reference signal. Depending on the mode desired, either the volume flow reference signal or the pressure flow reference signal or the greater of the two becomes a flow reference signal that is used to generate a control valve position signal based on a predetermined relationship. This signal is then used to vary the valve orifice area and correct the flow rate.

22 Claims, 4 Drawing Sheets

FLOW CONTROL SYSTEM FOR MEDICAL VENTILATOR

BACKGROUND OF THE INVENTION

This invention relates generally to the field of medical ventilators. More particularly, it relates to a system for controlling the flow of inspiratory gas in a volume-cycled, pressure-limited ventilator.

Volume-cycled, pressure-limited ventilators (commonly called "volume" ventilators), have become well-established for life support and respiratory therapy, particularly for adults. While the volume ventilator has assumed numerous forms, in general it operates by providing a predetermined volume of respiratory gas (air or oxygen-enriched air, typically with added water vapor) to the patient during the inspiratory phase of each breathing cycle. Specifically, the volume ventilator delivers the gas in accordance with a predetermined flow rate function, wherein the delivered flow rate is integrated over time until a predetermined volume is delivered.

A typical volume ventilator includes a flow control valve that is electronically or pneumatically actuated to produce an instantaneous flow rate throughout the inspiratory phase that corresponds with a preselected flow rate function, as set by the operator. An example of such a flow control system is disclosed in U.S. Pat. No. 4,527,557—DeVries et al., assigned to the assignee of the invention disclosed and claimed herein. The system disclosed in the DeVries et al. patent comprises a flow control valve actuated by a stepper motor that is controlled by a control signal generated by a microcomputer. The microcomputer generates the control signal by comparing an instantaneous flow rate signal produced by a flow transducer with a flow rate value required by a flow rate function stored in the microcomputer's memory. Other volume ventilator systems using a signal from a flow sensor to actuate a flow control valve are disclosed in the following U.S. Pat. Nos.: 3,923,056—Bingmann et al.; 3,961,627—Ernst et al.; 3,972,327—Ernst et al.; and 4,928,684—Breitenfelder et al.

The system disclosed in the above-mentioned DeVries et al. patent exemplifies the use of a real time flow rate-indicative signal, generated by a flow transducer, as a feedback signal, wherein the instantaneously sensed flow rate is the parameter whose value is compared with the stored nominal value to generate the stepper motor control signal. The use of a closed-loop feedback system, including a stepper motor under the command of a microprocessor, to operate the flow control valve allows the system to achieve a relatively high degree of precision over a wide range of flow rates, with the ability to accommodate a wide variety of flow rate patterns.

While the system described above has provided highly satisfactory levels of performance, there has been a desire to improve responsiveness and reliability beyond the limitations inherent in state-of-the-art flow transducers. For example, instead of sensing flow rate directly, a value for the instantaneous flow rate can be calculated by measuring the pressure drop across a flow orifice of known area. State-of-the-art pressure transducers can achieve high levels of accuracy and reliability, and a variety of means can be used to determine the size of a variable orifice, either directly or indirectly, with precision. With state-of-the-art high speed microprocessors, a highly precise value for the instantaneous flow rate can be obtained in real time or near real time.

The general method of measuring a fluid flow rate as a function of the sensed pressure differential across an orifice is well-known in the fluid metering art, as exemplified by the following U.S. Pat. Nos.: 3,055,389—Brunner; Re. 29,383—Gallatin et al.; and 4,277,832—Wong. This general method has also been employed to measure air flow in air conditioning and room ventilation ducts, as shown in U.S. Pat. No. 4,026,321 Kahoe et al. and U.S. Pat. No. 4,796,651—Ginn et al.

Medical ventilators have likewise employed flow control systems in which an instantaneous flow rate value is calculated from a measured value for pressure and a known or measured value for flow orifice size. Examples of such ventilators are disclosed in U.S. Pat. No. 4,637,385—Rusz and U.S. Pat. No. 4,883,051—Westenkow et al.

As far as is known, despite the desire for ever-increasing reliability, responsiveness, and flexibility in flow control capability in volume ventilators, the prior art has not contemplated the precision actuation of a ventilator flow control valve using a stepper motor under the command of a microprocessor, wherein the microprocessor transmits a correction or control signal to the stepper motor in response to signals indicative of (a) the varying differential pressure across a variable flow orifice in the valve, and (b) the effective flow area of the valve orifice.

SUMMARY OF THE INVENTION

Broadly, the present invention is a system for controlling the flow of inspiratory gas in a volume ventilator, comprising a variable-orifice flow control valve actuated by a stepper motor under the command of a microprocessor, wherein the microprocessor receives signals representing (a) gas pressure upstream from the valve, (b) gas pressure downstream from the valve, (c) gas temperature downstream from the valve, and (d) effective flow orifice area. The microprocessor calculates a measured instantaneous actual flow rate value as a function of these parameters, and then logic circuitry compares the calculated actual value with a desired value based on the controls set by the operator. The resultant flow signal is used to generate a control valve position signal, in accordance with a predetermined relationship, that is used to control the stepper motor so as to drive the valve mechanism to a position wherein the orifice yields an instantaneous flow rate substantially equal to the desired flow rate value. Additional feedback loops are used to improve accuracy and response times.

In effect, the system uses both the effective flow orifice area and the differential pressure across the orifice as active feedback control parameters, whereby the differential pressure across the orifice is periodically detected, and the resulting representative signal is used in a feedback loop, along with a signal representing the effective orifice area, to adjust the orifice area to provide the nominal instantaneous flow rate value.

In a specific preferred embodiment, the flow control valve comprises a housing with a flow orifice between an inlet and an outlet. The orifice defines a seat for a valve element that is lifted off of the seat by a cam-driven pushrod. The cam, in turn, is rotated by the shaft of the stepper motor. The effective flow area of the orifice is proportional to the distance between the valve element and the seat.

The microprocessor receives the upstream gas pressure signal from a first pressure transducer located upstream from the valve. The downstream gas pressure signal is received from a second pressure transducer located downstream from the valve. The downstream pressure sensed by the second pressure transducer may advantageously be the airway proximal pressure of the patient. A thermistor provides the downstream gas temperature signal received by the microprocessor.

An electrically erasable programmable read only memory (EEPROM) stores a look-up table of values representing the effective orifice area as a function of values indicating the angular position of the stepper motor shaft. Optical sensors operatively associated with the stepper motor shaft generate signals representing the extreme open and closed positions of the valve element as reference points for a logic circuit that provides a signal indicative of the angular position of the shaft. The microprocessor addresses the EEPROM with the shaft position signal to obtain the corresponding value for the effective orifice area. The microprocessor then computes the actual volumetric flow rate from the values it receives for upstream pressure, downstream pressure, downstream temperature, and effective orifice area, using a formula stored in its memory. The calculated flow rate, which is corrected for standard temperature and atmospheric pressure, is thus the instantaneous flow rate actually delivered to the patient through the flow control valve.

The calculated delivered flow rate value is compared, in a logic circuit, with a desired flow rate value that is derived from the settings of parametric controls by the operator. The comparison yields a difference signal that is converted to a valve position signal, in accordance with a predetermined relationship. This valve position signal is supplied as a control signal to control circuitry for the stepper motor, whereby the stepper motor is actuated to drive the valve element to a position that provides a flow rate substantially equal to the desired flow rate.

The present invention offers significant advantages over prior art ventilator flow control systems. For example, the use of gas pressure and valve position sensors to obtain a calculated flow rate value, and the use of differential pressure and valve position as feedback parameters, result in greater reliability in flow rate control than has heretofore been possible in systems that measure flow rate directly, due to limitations in the reliability of flow rate sensors. Moreover, this precise control is obtainable throughout a wide range of flow rates, and for a wide variety of flow rate patterns. Thus, the system is adaptable for use in numerous different applications and in all commonly-used ventilation modalities. The mechanical aspects of the system are relatively simple, for improved reliability, and, as will be seen, is easily calibrated. Moreover, the use of predetermined relationships between valve orifice area stepper motor position, and between stepper motor position and flow rate, coupled with the multiple feedback control mechanism, allows the invention to achieve very rapid response times for gross adjustment of the flow rate, while providing for fine adjustment of the flow rate to a high degree of accuracy.

These and other advantages will be more fully appreciated from the detailed description that follows.

DETAILED DESCRIPTION OF A PREFERRED EMBODIMENT OF THE INVENTION

Figure 1:
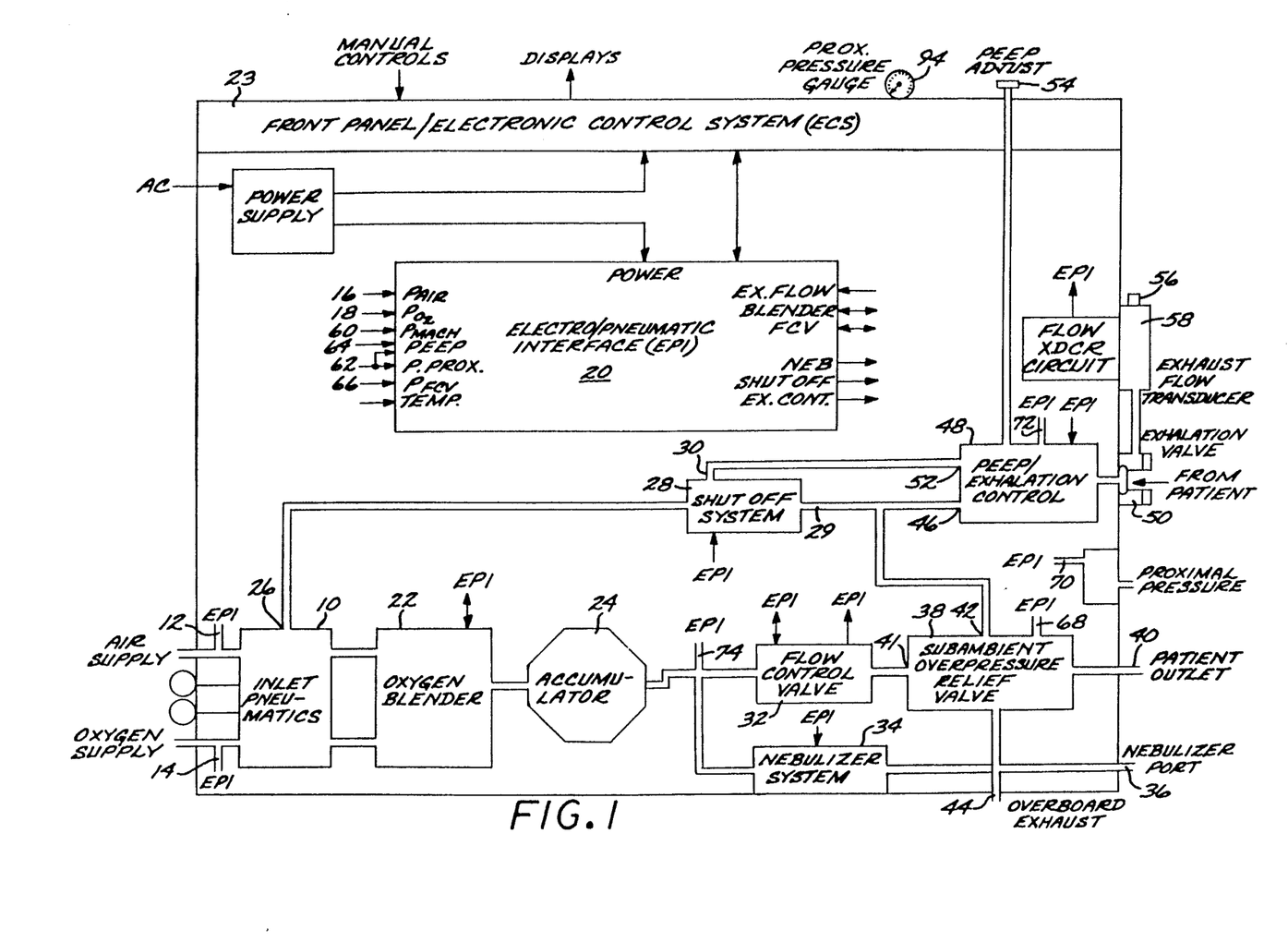
FIG. 1 is a functional schematic diagram of a volume ventilator incorporating a flow control system in accordance with the present invention.

A volume ventilator incorporating a preferred embodiment of the present invention is illustrated schematically in FIG. 1.

The ventilator receives air and oxygen from pressurized supplies. The air and oxygen are filtered and regulated to 18 psig by conventional means, well-known in the art, illustrated schematically by a functional box 10, labeled "Inlet Pneumatics System". A description of a typical embodiment of the inlet pneumatics system is found in U.S. Pat. No. 4,527,557—DeVries et al., assigned to the assignee of the present application, the disclosure of which is incorporated herein by reference. The inlet pneumatics system 10 includes an air pressure tap 12 and an oxygen pressure tap 14, which lead, respectively, to an air pressure port 16 and an oxygen pressure port 18 of an electro-pneumatic interface (EPI) unit 20, to be described below.

From the inlet pneumatics system 10, the air and oxygen are fed to a blender 22, preferably of a type similar to that disclosed and claimed in U.S. Pat. No. 4,602,653—Ruiz-Vela et al., assigned to the assignee of the present application, the disclosure of which is incorporated herein by reference. The proportion of the oxygen in the blended gas may be varied between 21% and 100% by the blender 22, based on the oxygen percentage set on the control panel of the ventilator. An electronic control system (ECS) 23 converts the mechanical selection of the blend by the operator into an electrical signal, by conventional means, which signal is fed to the EPI unit, where it is conditioned and fed to the control mechanism for the blender 22. The air/oxygen mixture (which may now be referred to as "inspiratory gas") is then fed into an accumulator 24.

The inlet pneumatics system 10 also has a drive gas outlet 26, through which drive gas is provided for the operation of several ventilator subsystems, as will be discussed below. The drive gas is conducted through a shut-off system 28, described more fully below, which has a low pressure outlet 29 and a high pressure outlet 30. Drive gas from the low pressure outlet 29 is regulated to about 2 psig, while gas from the high pressure outlet 30 remains at approximately 18 psig.

From the accumulator 24, the major portion of the inspiratory gas is directed to a flow control valve 32, which will be described in detail below. A small portion of the accumulator outflow may optionally be tapped for direction to a conventional nebulizer system 34, which is controlled by a signal received from the EPI unit 20. The tapped flow from the nebulizer system 34 is directed to a nebulizer port 36. The major portion of the accumulator outflow is directed through the flow control valve 20, then through a subambient/overpressure relief ("SOPR") valve 38, to a patient outlet 40. From the patient outlet 40, the inspiratory gas is conducted to the patient through a conventional patient circuit (not shown), after passing through a bacterial filter (not shown) and an optional humidifier (not shown).

The SOPR valve 38 performs a dual function: (1) It allows the patient to breathe ambient air in the event of ventilator failure; and (2) it acts as a relief valve to limit the maximum pressure delivered by the ventilator. The SOPR valve 38 has an inspiratory gas inlet port 41 that receives inspiratory gas from the flow control valve 32, and, in normal operation, passes the gas through to the patient outlet 40. The SOPR valve 38 has a first reference pressure inlet 42 that receives 2 psig drive gas pressure from the low pressure outlet 29 of the shut-off system 28. The 2 psig pressure acts as a reference pressure on one side of a spring-biased diaphragm (not shown), the other side of which is exposed to the gas flow received from the flow control valve. The diaphragm's pressure ratio is selected such that when the inspiratory gas pressure received from the flow control valve 32 exceeds about 175 cmH$_2$O, the diaphragm opens an internal valve passage (not shown) from the inspiratory gas inlet port 41 to an overboard exhaust port 44, thereby relieving the excess pressure.

Should the pressure at the first reference pressure inlet 42 fall to near zero (indicating a ventilator failure, due to, for example, loss of power or a failure of the inlet pneumatics system 10), the diaphragm opens under the force of its biasing spring (not shown), opening the above-mentioned internal passage to provide direct communication between the patient outlet 40 and the overboard exhaust port 44, thereby allowing the patient to inhale ambient air.

As mentioned above, the shut-off system 28 provides the 2 psig reference pressure to the SOPR valve 38 through the low pressure outlet 29. This reference pressure is also directed to a second reference pressure inlet port 46 in a PEEP/exhalation control subsystem 48. ("PEEP" is an acronym for Positive End Expiratory Pressure.) The PEEP/exhalation control subsystem 48 controls the operation of an exhalation valve 50, as will be described below. The 18 psig drive gas from the high pressure outlet 30 of the shut-off system 28 is delivered to a high pressure inlet port 52 in the PEEP/exhalation control subsystem 48.

The shut-off system 28, which is under the control of the EPI unit 20, includes a solenoid valve (not shown), having an inlet that receives drive gas from the inlet pneumatics system 10, and an outlet that communicates substantially directly with the high pressure outlet 30, and through a low pressure regulator (not shown) with the low pressure outlet 29. During normal operation of the ventilator, the solenoid is energized, passing 18 psig drive gas through to the high pressure outlet 30 and to the low pressure regulator, the latter dropping the pressure to 2 psig for passage through the low pressure outlet 29.

If ventilator power is lost, the solenoid valve in the shut-off system 28 closes, cutting off drive gas to the PEEP/exhalation control subsystem 48, and thus depressurizing the exhalation valve 50. With no drive pressure applied to it, the exhalation valve 50 remains fully open, allowing the patient to exhale unimpeded. Closure of the shut-off system 28 also opens the passage in the SOPR valve 38 between the patient outlet 40 and the overboard exhaust port 44, as described above, thereby allowing unimpeded inhalation of ambient air.

The PEEP/exhalation control subsystem 48 and the exhalation valve 50 are similar to those disclosed in the above-mentioned U.S. Pat. No. 4,527,557—DeVries et al., and thus only a brief description is needed here. The purpose of these components is twofold: (1) to close off the expiratory limb of the patient circuit during inhalation and open it during the exhalation; and (2) to maintain a selected PEEP level during exhalation. The exhalation valve 50, which is controlled by a signal from the EPI unit 20, also acts as a check valve, preventing inhalation through the expiratory leg of the patient circuit.

The PEEP/exhalation control subsystem 48 includes a variable-orifice needle valve (not shown), the upstream side of which receives 18 psig drive gas from the high pressure outlet 30 of the shut-off system 30. A jet pump (not shown), downstream from the needle valve, creates a static pressure that is applied to the ventilator side of the exhalation valve 50 to establish the PEEP. The level of PEEP is selected by varying the orifice of the needle valve by means of a PEEP adjustment control 54 on the control panel of the ventilator.

During exhalation, the patient's exhaled breath is conducted from the exhalation valve 50 to an exhalation outlet 56 through an exhalation flow transducer 58, preferably of the "hot wire" type. The exhalation flow transducer 58 generates an analog electrical output signal that is conditioned (i.e., digitized, amplified, and temperature-compensated) by associated flow transducer circuitry 59, before being fed into the EPI unit 20, which, in turn, produces an output signal directed to the ECS 23, which includes means (not shown) for integrating the signal over time to generate a visual display (not shown) of the exhalation volume.

Figure 2:
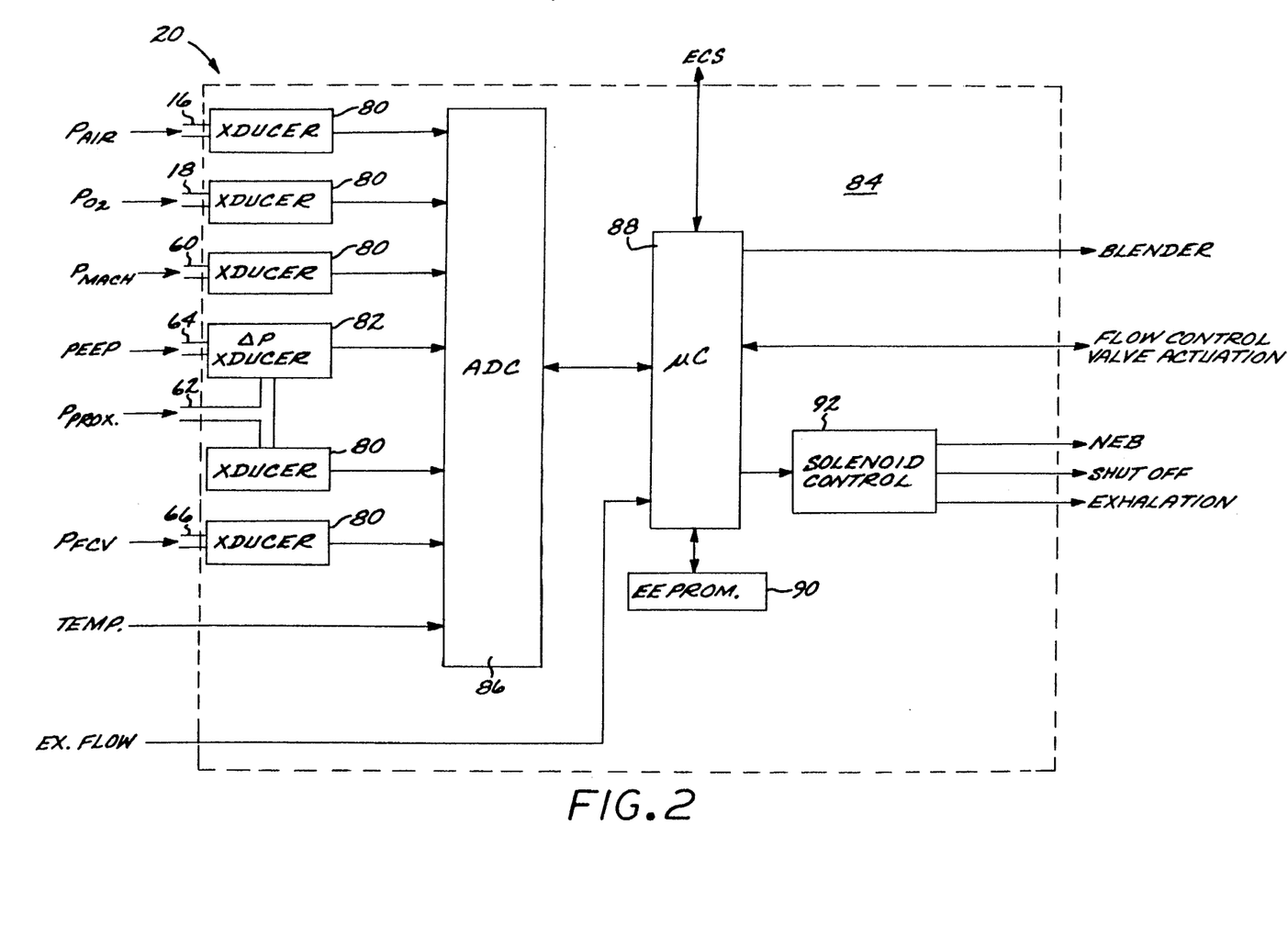
FIG. 2 is a functional schematic representation of the electro-pneumatic interface unit employed in the ventilator of FIG. 1.

The EPI unit 20 is best understood with reference to FIG. 2. One major purpose of the EPI unit is to provide a clear interface between the ECS 23 and the pneumatic components of the ventilator. From the manual controls of the ECS 23, the EPI unit 20 receives signals representing the operator-selected values for the operational parameters, such as flow rate, oxygen concentration, and valve states. These signals are communicated to the EPI unit 20 every 10 milliseconds. Based on these signals, the EPI unit 20 commands the various valves (e.g., the blender 22, the flow control valve 32, and the PEEP/exhalation control subsystem 48) to assume their correct positions or states.

Another major function of the EPI unit 20 is to receive pneumatic and electrical signals representing pressures, temperatures, and flow rates within the ventilator, and to process these signals for use in controlling the ventilator, either automatically (i.e., by servo-control mechanisms), or manually (i.e., through the ECS 23).

As shown in FIG. 2, the EPI unit 20 includes several pneumatic input ports. Among these are the previously mentioned air pressure port 16 and the oxygen pressure port 18. Also included are a machine pressure port 60, a proximal pressure port 62, a PEEP port 64, and flow control valve pressure port 66. The machine pressure port 60 receives a static pressure from a machine pressure tap 68 at the downstream side of the SOPR valve 38. The proximal pressure port 62 receives a static pressure from a proximal pressure tap 70 on the ventilator side of the patient connector (not shown) that couples the patient to the patient circuit. The PEEP port 64 receives the PEEP from a PEEP tap 72 in the PEEP-/exhalation control subsystem 48. The flow control valve pressure port 66 receives a static pressure from a flow control valve pressure tap 74 located on the upstream side of the flow control valve 32.

The air pressure port 16, the oxygen pressure port 18, the machine pressure port 60, the proximal pressure port 62, and the flow control valve pressure port 66 each communicates with an associated miniature gage pressure transducer 80. The proximal pressure port 62 also communicates with one side of a miniature differential pressure transducer 82, the other side of which is in communication with the PEEP port 64. The transducers 80, 82 are preferably of a type marketed as the "16PC Series" by the Micro Switch Division of Honeywell, Inc. Transducers of this type are sensitive enough for the purposes of this invention, with a suitable pressure range, and yet are small enough for mounting on a printed circuit board 84 with the other electronic components, described below, of the EPI unit.

Each of the gage transducers 80 produces an analog electrical output signal representing the value of the pressure applied to that transducer's associated port. The differential transducer 82 produces an analog electrical output signal representing the value of PEEP minus the proximal pressure; this differential signal may be termed "$P_{DELTA}$", and usually has a negative value. The analog signals are fed into an analog-to-digital converter (ADC) 86, which includes suitable amplification circuitry (not shown). After the signals are digitized and amplified, they are fed into a microcomputer 88, which also receives signals from the ECS 23, the blender 22 and the exhalation flow transducer circuitry 59. Because the transducers 80 and 82 are mounted directly on the board 84, the transmission distances of their analog output signals to the ADC 86 are minimized, thereby rendering them less susceptible to noise (e.g., EMI) from external sources. Calibration factors for the pressure transducers 80, 82 are advantageously stored in an EEPROM 90 that is electronically coupled to the microcomputer 88.

By way of specific example, the microcomputer 88 may advantageously comprise a microcontroller (such as a Motorola 68HC05 microcontroller, or a substantial equivalent thereof) and a 4 MHz crystal, with the following on-chip functions: 176 bytes of random access memory (RAM), 7584 bytes of Read Only Memory (ROM), three 8-bit I/O ports, a serial peripheral interface port (for communication with the ADC 86 and the exhalation flow transducer circuitry 59), a serial communication interface port (for communicating with the ECS 23), and an 8-bit timer.

Digital output signals from the microcomputer 88 are used to control the blender 22, the nebulizer system 34, the shut-off system 28, the PEEP/exhalation control subsystem 48, and the flow control valve 32, the control of the flow control valve being described in detail below.

The signals from the above-described pressure transducers have the following significance:

The air and oxygen pressure signals indicate proper operation of the inlet pneumatic system 10. An air or oxygen pressure below a predetermined threshold indicates a gas failure, as a result of which the microcomputer 88 is signaled to trigger an alarm (not shown) and to actuate the shut-off system 28, as described above, through a solenoid control circuit 92, of a type that is well-known in the art.

The machine pressure signal represents the inspiratory gas pressure in the ventilator downstream from the flow control valve 32. The proximal pressure signal represents the pressure on the ventilator side of the patient connector. This signal is used, as will be explained below, to calculate the flow rate of inspiratory gas delivered to the patient through the flow control valve 32. It may also be used as an input signal to actuate a proximal pressure display, such as a gage 94 (FIG. 1) or an external pressure monitor (not shown). The flow control valve pressure signal represents the inspiratory gas pressure on the upstream side of the flow control valve 32. This signal is used, along with the proximal pressure signal, to calculate the flow rate through the flow control valve 32, as will be explained below.

The $P_{DELTA}$ signal represents the difference between the PEEP and the proximal pressure. This signal is used as a feedback control signal for controlling the flow control valve 32 when the ventilator is in the pressure control, pressure support, or pressure augmentation mode, as will be explained below.

Figure 3:
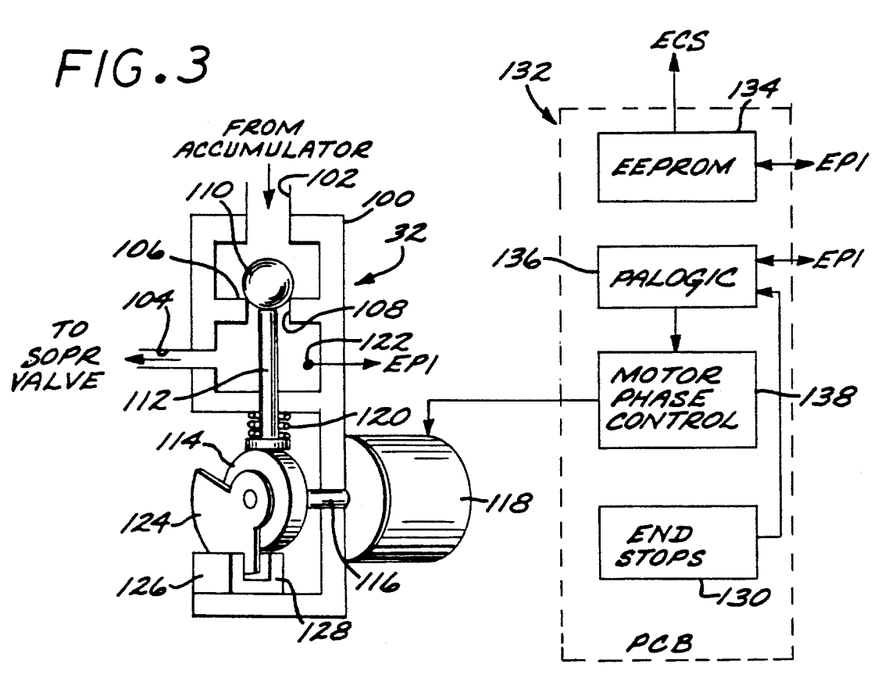
FIG. 3 is a semi-schematic representation of the flow control valve, the stepper motor that actuates the valve, and the circuitry that controls the motor, as used in the present invention.

The flow control valve 32, illustrated in FIG. 3, comprises a housing 100 having a gas inlet 102 that receives inspiratory gas from the accumulator 24, and a gas outlet 104 that delivers the gas to the SOPR valve 38. Between the inlet 102 and the outlet 104 is a valve seat 106 defining a valve orifice 108, the effective flow area of which is varied by a poppet valve element 110, preferably spherical in form, as shown. The position of the valve element 110 relative to the valve seat 106, and thus the effective flow area of the valve orifice 108, is controlled by a rod 112 that is journaled, by suitable bearings (not shown), for axial movement within the valve housing 100. One end of the rod 112 engages the valve element 110, while the other end is engaged by an asymmetrical cam 114 that is mounted on a shaft 116 of a stepper motor 118. The rod 112 is advantageously maintained in engagement with the cam 114 by a coil spring 120.

In terms of its overall mechanical structure, the flow control valve 32 is similar to the flow control valve disclosed in the above-mentioned U.S. Pat. No. 4,527,557—DeVries, except that in the prior art valve, the valve element seats against the downstream side of the flow orifice, while in the flow control valve 32 employed in the present invention, the valve element 110 seats against the upstream side of the orifice 108. In addition, the flow control valve 32 of the present invention uses the spring 120 to assure that the rod 112 follows the cam 114, while the prior art device uses gas pressure for this purpose. It should be noted that a flow control valve of the type disclosed in the DeVries patent can be used in a flow control system in accordance with the present invention, without departing from the spirit and scope of the invention.

The valve housing 100 contains temperature sensing means, such as a thermistor 122, downstream from the valve orifice 108. The thermistor 122 generates an analog electrical signal representing the temperature of the inspiratory gas, and this signal is then inputted to the EPI unit 20, and, more specifically, to the ADC 86.

The stepper motor 118 is a unipolar, four-phase motor, with a resolution of at least about 0.9 degrees of rotation per half step, and an effective rotational speed of approximately 1100 half steps per second. Through the shaft 116, the cam 114 and the rod 112, the motor 118 drives the valve element 110 between a fully closed position (corresponding to zero half steps of the motor) and a fully open position (corresponding to between 112 and 119 half steps of the motor, or approximately 101 to 107 degrees of rotation of the shaft 116. The zero flow (fully closed) position and the full flow (fully open) position are the end limits of rotational movement of the motor, as determined by an optical encoder element 124 that is coupled to the shaft 116, and that is configured to interrupt a light beam (not shown) at the above-mentioned limits of rotational travel. The light beam may be transmitted from optical emission means, such as an LED 126, to a photodetector 128. Interruption of the beam thus causes the photodetector 128 to generate an "end stop" signal, represented schematically in FIG. 3 by a functional box 130, labeled "End Stops".

The motion of the stepper motor 118, and thus the position of the flow control valve element 110, is controlled by an electronic valve actuation subsystem 132 in the following manner:

A "position-to-area" look-up table of values representing the effective flow orifice area as a function of the angular position of the stepper motor shaft 116 (in terms of the number of stepper motor half steps from the zero end stop) is stored in a flow control EEPROM 134, which is preferably a 256×8 bit device, such as a XICOR model X2402. The number of half steps that the motor 118 has stepped through from the zero end stop is determined by a second microcomputer (described below) in the ECS 23, and transmitted to the EPI microcomputer 88.

A programmable array logic device 136 (such as the device marketed by Advanced Micro Devices under the trademark ("PAL16R4", or the substantial equivalent thereof) generates a control signal for controlling the motor 118 in response to signals received from the microcomputer 88 and the end stop mechanism 130. This motor control signal is inputted to a motor phase controller 138 (such as the SGS Model L6506 current controller, or the substantial equivalent thereof), which provides pulse width modulation current regulation to the motor 118 to move it the appropriate number of steps in the appropriate direction. The half step number determined by the ECS microcomputer is used in the position-to-area look-up table stored in the flow control EEPROM 134 to determine the effective flow orifice area corresponding to that half step number from the look-up table stored therein. The looked-up flow orifice area value is then temporarily stored in the microcomputer's RAM.

The position-to-area look-up table in the EEPROM 134 is unique to each flow control valve and its associated stepper motor. Thus, the PC board on which the EEPROM 134 is mounted is physically attached to the valve/stepper motor assembly, and the EEPROM is loaded with a look-up table that is empirically derived for the valve/motor assembly to which it is attached. Thus, in effect, each valve is pre-calibrated during manufacture by the loading of its unique look-up table, and no further calibration is necessary. Should the valve and/or motor later need to be replaced, a new valve/motor/PC board assembly is installed, already calibrated by the loading of the look-up table.

Figure 4:
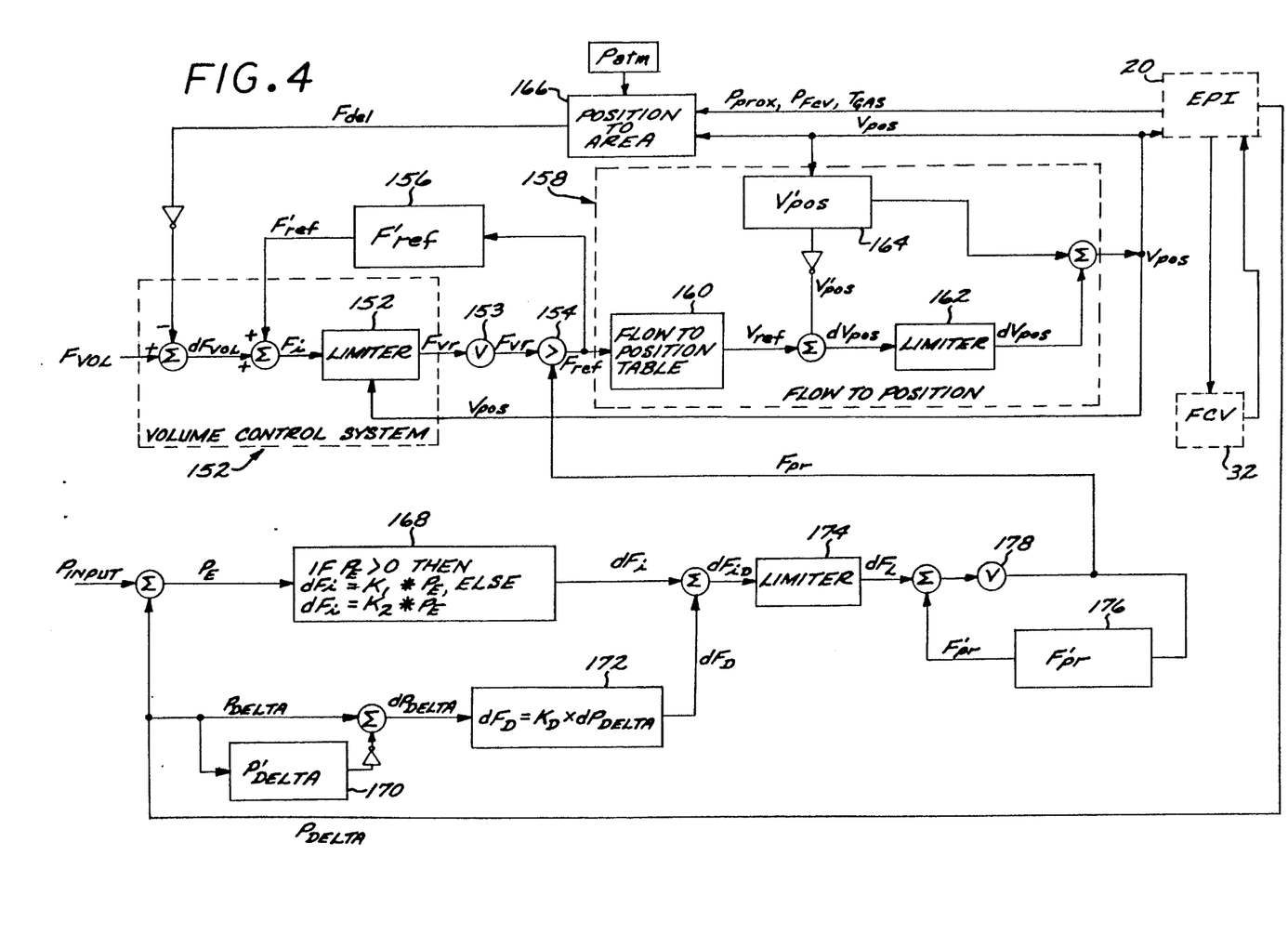
FIG. 4 is a schematic flow chart diagram showing the operation of the electronic control system microcomputer used to control the flow of inspiratory gas in the ventilator of FIG. 1.

The operation of the ECS microcomputer, discussed above, is illustrated in the schematic flow chart diagram of FIG. 4. In a preferred embodiment of the invention, the ECS microcomputer comprises an Intel 80188 NMOS microcontroller and a 20 MHz crystal oscillator, with the following on-chip functions: three 16-bit counter/timers, two DMA channels, an interrupt controller, a clock generator, and programmable memory/peripheral chip select logic. The ECS microcomputer also includes an 8K×8 CMOS static RAM, a 64K×8 EPROM (containing the control software), and three 10-bit digital-to-analog converters (DACs) (for outputting analog flow rate, volume and pressure signals in real time).

The EPROM of the ECS microcomputer has stored within it a set of algorithms for calculating an instantaneous actual ("real time") volumetric flow rate value for the "delivered" flow through the flow control valve 32. The algorithms, in essence, solve the following equation for the actual volumetric "delivered" flow rate F, with standard temperature, ambient pressure correction:

$$F = \frac{A * RKT * P_1 * N}{SQRT(T_{gas}) * P_{atm}}, \quad (1)$$

where A is the effective flow orifice area, RKT is a correction factor that is a function of the oxygen concentration, $P_1$ is the pressure upstream from the flow control valve (flow control valve pressure), $P_2$ is the pressure downstream from the flow control valve (proximal pressure), $T_{gas}$ is the inspiratory gas temperature in the flow control valve (measured on the Rankine scale), N is a weighted flow ratio (which is a function of the ratio of $P_2$ to $P_1$), and $P_{atm}$ is atmospheric pressure (which may be selected by the operator to approximate the average barometric pressure of the geographic location of the ventilator).

The values of the correction factor RKT as a function of the percentage of oxygen in the inspiratory gas blend (21% to 100%) are contained in a look-up table stored in the ECS unit EPROM. The values for RKT are derived from the following equation:

$$RKT = R*K*T_a*0.9833 \quad (2)$$

where $T_a$ is an assumed value for ambient temperature, namely 537° R, 0.9833 is a conversion constant to convert the units of the RKT factor to liters per minute (lpm), and R and K are gas factors that are derived from the following equations:

$$R = \frac{Vf_a * M_a * R_a}{M} + \frac{Vf_o * M_o * R_o}{M} \quad (3)$$

$$K = \frac{Vf_a * M_a * K_a}{M} + \frac{Vf_o * M_o * K_o}{M} \quad (4)$$

where $Vf_a$ is a fraction indicating the proportion of air in the blended mixture, varying from 0 (pure oxygen) to 1 (pure air); $Vf_o$ is a fraction indicating the proportion of oxygen in the mixture, varying from 1 (pure oxygen) to 0 (pure air); $M_a$ is a constant indicating the average molecular mass of normal ambient air (28.96); $M_o$ is a constant indicating the molecular mass of oxygen (32.00); $R_a$ and $K_a$ are empirically derived gas constants for air; and $R_o$ and $K_o$ are analogous, empirically derived gas constants for oxygen. The parameter M is the average molecular mass of the gas mixture, and its value is obtained from the following equation:

$$M = (Vf_o * M_o) + (Vf_a * M_a) \quad (5)$$

Likewise, the values of N are contained in a look-up table stored in the ECS unit EPROM. These values are derived from the following equation:

$$N = [(P_2/P_1)^{G1}/G3 - (P_2/P_1)^{G2}/G3]^{\frac{1}{2}} \qquad (6)$$

where G1, G2, and G3 are empirically derived constants having the approximate values of 1.429, 1.714, and 0.067, respectively.

The value for proximal pressure is derived from the gage pressure transducer 80 associated with the proximal pressure port 62 in the EPI unit 20. The flow control valve pressure value is derived from the gage pressure transducer 80 associated with the flow control valve pressure port 66 in the EPI unit 20. As discussed above, signals representing these pressure values are transmitted by the transducers to the microcomputer 88, after conditioning by the ADC 86. The inspiratory gas temperature $T_{gas}$ is represented by a temperature signal received by the microcomputer 88 from the thermistor 122 in the flow control valve 32, after this temperature signal has been conditioned by the ADC 86.

As explained in detail below, in the volume control mode of ventilator operation, the calculated volumetric flow rate value (the "flow signal") is compared, in logic circuitry contained in the ECS 23, with a desired flow rate value ("volume input signal"), based on the control settings selected by the operator (either directly, or as a function of other parameters). The comparison yields a difference or correction signal. This correction signal is used to generate a flow control valve position signal which is eventually supplied as a pulse train to the programmable array logic device 136. The pulse train determines the number of half steps the motor must turn, and a directional bit is included to control the direction of rotation. In response to the pulse train, the programmable array logic device 136 generates a motor control signal for the stepper motor 118, whereby the motor is actuated to drive the valve element 110 to a position that provides a flow rate substantially equal to the desired flow rate.

. The logic circuitry that provides the aforementioned function is illustrated schematically in FIG. 4. Starting in the upper left of the schematic, a desired volume input signal $F_{vol}$ is generated in the ECS 23, in response to the operator's selection (via manual controls) of such respiratory parameters as end tidal volume, breath rate, inspiratory waveform, and the ratio of inspiratory time to expiratory time (I:E ratio). This $F_{vol}$ signal is the input signal to a volume control system 150, in which it is algebraically summed with an inverted delivered flow signal $F_{del}$, which, as will be explained below, indicates the actual instantaneous volumetric flow rate through the flow control valve 32. The difference between $F_{vol}$ and $F_{del}$ is a flow correction signal $dF_{vol}$, which is summed with a previously stored flow reference signal value $F'_{ref}$, the derivation of which will be made clear below. This sum yields an intermediate volume reference signal $F_i$.

The circuitry of FIG. 4 is designed to correct the position of the flow control valve 32 every 10 milliseconds. As mentioned above, the stepper motor 118 has an effective rotational speed of about 1100 half steps per second. Therefore, the stepper motor can be expected to rotate no more than 11 half steps during each valve position correction cycle. Accordingly, a first limiting algorithm 152 is provided that receives the intermediate volume reference signal $F_i$ and a current valve position signal $V_{pos}$. The first limiting algorithm 152 determines upper and lower flow rate limits that would require the stepper motor to rotate 11 half steps in either direction from its current position, as indicated by the value of $V_{pos}$. The first limiting algorithm 152 then compares the value of $F_i$ with the upper and lower flow rate limits. If the $F_i$ value is between the limits, the first limiting algorithm 152 outputs the actual $F_i$ value as a volume reference signal $F_{vr}$. If the value is above the upper limit, the first limiting algorithm outputs a $F_{vr}$ value that is equal to the upper limit. If the inputted $F_i$ value is below the lower limit, the output is equal to the lower limit.

If the ventilator is operated in the volume control mode, a flow control enable switch 153 is turned "ON". The volume reference signal $F_{vr}$ is then inputted to a comparator 154, the purpose of which will be explained below. The output of the comparator 154 is a flow reference signal $F_{ref}$. The value of $F_{ref}$ is then stored in a first random access memory (RAM) sector 156, so that its immediately preceding value $F'_{ref}$ can be summed with the flow correction signal $dF_{vol}$ to produce the intermediate volume reference signal $F_i$, as described above.

The flow reference signal $F_{ref}$ is then inputted to a flow-to-position subsystem 158, in which it is used to address a flow-to-position look-up table 160, stored in the ECS EPROM. The flow-to-position look-up table 160 contains values for stepper motor positions corresponding to each increment of the flow rate reference signal $F_{ref}$, based on predetermined conditions, and thereby produces as its output a flow control valve position reference signal $V_{ref}$. The position reference signal $V_{ref}$ is algebraically summed with an inverted, previously stored position signal value $V'_{pos}$, the derivation of which will be made clear below, to yield a position error signal $dV_{pos}$. This signal is then inputted to a second limiter circuit 162, which limits the value of the position error signal $dV_{pos}$ to one that will not drive the stepper motor 118 more than 11 half steps in either direction from its current position.

The position error signal $dV_{pos}$ is then algebraically summed with the valve position signal $V'_{pos}$. The resulting value is the current value position signal $V_{pos}$, which is stored in a second RAM sector 164, from which the value $V'_{pos}$ is generated for inversion and summing with the position reference signal $V_{ref}$ to produce the position error signal $dV_{pos}$, as described above.

As described above, a look-up table of flow orifice area values as a function of stepper motor position (number of steps from the zero end stop) is stored in the EEPROM 134 associated with the flow control valve 32 (FIG. 3). This look-up table may be called a "position-to-area" look-up table, and it is represented in FIG. 4 by a functional box 166. The ECS microcomputer addresses the position-to-area look-up table 166 to read the effective orifice area value A corresponding to the value of the position signal $V_{pos}$. This value is then used by the microcomputer to calculate the actual flow rate through the flow control valve 32, using Equation (1) above, with values for RKT, N, $P_1$, $T_{gas}$, and $P_{atm}$ either inputted or read from look-up tables, as described above. This calculated flow rate value is outputted as the delivered flow rate signal $F_{del}$.

The current valve position signal value $V_{pos}$ is transmitted to the EPI microcomputer 88 which, in turn, pulses the programmable array logic device 136 as described above. In response to these signal values, the programmable array logic device generates the motor control signal that causes the stepper motor to rotate the appropriate number of half steps (not more than 11) in the appropriate direction, corresponding to the difference between $V_{pos}$ and $V'_{pos}$. As the stepper motor is moving the valve element 110, and thus changing the effective flow orifice area, the valve position signal is conveyed to and converted by the position-to-area look-up table 166 to the effective orifice value A.

The ventilator is also capable of operation in pressure support and pressure control modes. Referring again to FIG. 4, the operator inputs a selected pressure value $P_{input}$, representing a desired inspiratory pressure. The $P_{input}$ value is summed with a value for $P_{delta}$ obtained from the EPI, as described above. The resulting sum is a pressure error signal $P_E$. The pressure error signal $P_E$ is processed, in the ECS microcomputer, using an algorithm in which the value of $P_E$ is multiplied by one of three factors, as follows: If the value of $P_E$ is positive, the multiplier is the operator-selected slope of the inspiratory pressure, represented in a functional box 168 in FIG. 4 by the symbol $K_1$. More specifically, the value of $K_1$ is the slope of an inspiratory pressure-versus-time curve selected by the operator by means of a control on the ECS. If the value of $P_E$ is zero or negative, then the multiplier is a constant $K_2$, having a value of 1.5 for adult patients, and 0.5 for pediatric patients. The appropriate value for $K_2$ is determined by an operator-actuated control in the ECS that provides for selecting either an "adult" mode or a "pediatric" mode. The result of this multiplication is a first flow correction signal $dF_i$.

The present value of the $P_{delta}$ signal is algebraically summed with an inverted, immediately preceding value $P'_{delta}$, stored in a third RAM sector 170. The resulting sum is a $P_{delta}$ correction signal $dP_{delta}$, which is then multiplied by a constant factor $K_D$, as illustrated in a function box 172. The factor $K_D$ is either 3 for an adult patient, or 1 for a pediatric patient, as selected by the operator. The result of this multiplication is a second flow correction signal $dF_D$.

The first flow correction signal $dF_i$ and the second flow correction signal $dF_D$ are algebraically summed, and the resulting sum $dF_{iD}$ is then operated on by a third limiting algorithm 174. As with the first and second limiting algorithms 152 and 162, respectively, described above, the purpose of the third limiting algorithm 174 is to limit the correction signal so that its value is such as to cause the stepper motor to be driven not more than 11 half steps in either direction. After the operation of the third limiting algorithm 174, the resulting limited flow correction signal $dF_L$ is used to generate a pressure control signal $F_{pr}$ by algebraically summing the limited flow correction signal $dF_L$ with the immediately preceding value $F'_{pr}$ of the pressure control signal, stored in a fourth RAM sector 176.

If the operator has selected either the pressure control mode or the pressure support mode, the volume control enable switch 153 is turned "OFF", and a pressure control enable switch 178 is turned "ON". This enables the pressure control signal $F_{pr}$ to address the flow-to-position table 160 as the flow reference signal $F_{ref}$ after passing through the comparator 154. Actuation of the flow control valve 32 then proceeds as described above in connection with the volume control mode.

Thus, in either the pressure control mode or the pressure support mode, the flow reference signal $F_{ref}$ is derived from the operator-selected inspiratory pressure value $P_{input}$, rather than from volume input signal $F_{vol}$, based on the operator-selected volumetric parameters used in the volume control mode.

The above described flow control mechanism allows for still another mode of ventilator operation, which may be termed the "pressure augmentation" mode. In the pressure augmentation mode, both the volume control enable switch 153 and the pressure control enable switch 178 are turned "ON". The comparator 154 then receives both the volume control signal $F_{vr}$ and the pressure control signal $F_{pr}$. The comparator 154 then determines which of these two signals has the larger value, and only the larger of the two is passed to the flow-to-position subsystem 158 for actuation of the flow control valve 32.

Thus, in the pressure augmentation mode, the operator can select a desired inspiratory pressure level $P_{input}$, a minimum end tidal volume, and a desired flow rate value $F_{vol}$. With the settings for these parameters selected so that the pressure control signal value $F_{pr}$ is normally greater than the volume control signal value $F_{vr}$, the patient can be ventilated essentially in the pressure control mode or pressure support mode. If, however, the actual inspiratory pressure exceeds the value of $P_{input}$ (due to reduced patient demand, increased airway resistance, or decreased lung compliance), the control signal $F_{vr}$ will become dominant, and then actuate the flow control valve so as to provide the flow rate required to achieve the selected end tidal volume. Thus, the patient is assured of receiving the operator-selected minimum end tidal volume. On the other hand, should the patient's demand be such as to create an inspiratory pressure below the value of $P_{input}$, the pressure control signal $F_{pr}$ will dominate, thereby actuating the flow control valve so as to provide the flow rate required to achieve the end tidal volume actually demanded by the patient.

Thus the subject invention provides a flow control system including a method for controlling the flow of gas that is particularly responsive to the input signal to the system. This input may be based on desired flow rate or desired effective pressure or the greater of the two. The equations disclosed and the factors used in processing the signals are those used in the preferred embodiment as used in a ventilator using the apparatus disclosed.

It is apparent that modifications may be made to the equations and/or factors used in processing which do not depart from the scope and spirit of the subject invention. For example, if a different motor or drive mechanism were to be used to vary the valve orifice area, the values used in the limiting algorithms may change. Also, the processing of the $P_{INPUT}$ and $P_{DELTA}$ signals may be changed to reflect desired pressure correction processing.

Additionally, while it has been disclosed that the valve reference signal is formed from the flow reference signal based on a predetermined relationship using a look up table, this predetermined relationship could alternatively be implemented by a microprocessor using the flow control valve pressure, the proximal airway pressure and an accurate relationship between position and orifice area.

What is claimed is:

1. A method for controlling the flow of a pressurized gas through a flow control valve in a pressurized gas conduit system in response to a volume input signal indicative of the desired flow rate comprised of the steps of:

generating a flow signal in a feedback loop indicative of the actual flow rate of gas flow through said flow control valve, subtracting said flow signal from said volume input signal to generate a correction signal which is indicative of the magnitude and direction of the difference between said flow signal and said volume input signal, forming a flow reference signal by adding said correction signal to the immediately previous flow reference signal, generating a control valve position signal from said flow reference signal based on a first predetermined relationship, inputting said control valve position signal to valve control means for varying the effective orifice flow area in said flow control valve in response to a control valve position signal to change the flow rate through said flow control valve, after a predetermined short time interval repeating the steps by first generating a new flow signal and subtracting it from the then current input signal so as to continually correct the flow rate through said flow control valve based on the difference between the actual flow rate through the flow control valve and the desired flow rate.

2. A method for controlling the flow of a pressurized gas as in claim 1 wherein said step of generating an electrical flow signal in a feedback loop indicative of the actual flow rate of gas flow through said flow control valve is comprised of the substeps of:

providing upstream and downstream electrical pressure signals from measurements of the pressures upstream and downstream of the flow control valve, providing a gas temperature electrical signal from a measurement of the temperature of the gas flowing through said flow control valve, using said control valve position signal to generate in accordance with a second predetermined relationship a valve orifice signal indicative of the effective orifice area within said flow control valve, and processing said upstream and downstream pressure signals and said gas temperature signal with said valve orifice signal.

3. A method as in claim 2 wherein said upstream and downstream pressure signals are generated from pressure transducers mounted on a common printed circuit board connected by conduits to their respective positions in the pressurized gas system.

4. A method for controlling the flow of a pressurized gas as in claim 1 wherein the substep of using said control valve position signal to generate a valve orifice signal includes using said control valve position signal in a look-up table defining the second predetermined relationship which has been derived by empirical testing.

5. A method as in claim 4 wherein said look up table has been specifically determined for the specific flow control valve being utilized.

6. A method as in claim 1 wherein said step of generating a control valve position signal from said flow reference signal based on a first predetermined relationship includes the substeps of:

generating a valve reference signal based on said first predetermined relationship, subtracting from said valve reference signal the current control valve position signal to form a valve position error signal, limiting the maximum magnitude of the valve position error signal to a predetermined maximum value, which value is based on the maximum correction to the change in orifice area that can be obtained within the predetermined short time interval, and adding said limited valve position error signal to the control valve position signal to form a new control valve position signal.

7. A method for controlling the flow of a pressurized gas through a flow control valve in a pressurized gas conduit system in response to an electrical input signal indicative of the desired flow rate comprised of the steps of:

providing upstream and downstream electrical pressure signals from pressure measurements upstream and downstream of the flow control valve, providing a gas temperature electrical signal from a measurement of the temperature of the gas flowing through said flow control valve, generating a valve orifice signal indicative of the effective orifice area within said flow control valve, processing said upstream and downstream pressure signals and said gas temperature signal together with said valve orifice signal to generate a flow signal in a feedback loop indicative of the actual flow rate of gas flow through said flow control valve, subtracting said flow signal from said volume input signal to generate a correction signal which is indicative of the magnitude and direction of the difference between said flow signal and said volume input signal, forming a flow reference signal by adding said correction signal to an immediately previous flow reference signal, generating a control valve position signal from said flow reference signal, inputting said control valve position signal to valve control means for varying the effective orifice flow area in said flow control valve in response to a control valve position signal to change the flow rate through said flow control valve, after a predetermined short time interval repeating the steps by first generating a new flow signal and subtracting it from the then current input signal so as to continually correct the flow rate through said flow control valve based on the difference between the actual flow rate through the flow control valve and the desired flow rate;

wherein the valve orifice signal is generated based on a second predetermined relationship using the then current control valve position signal.

8. A method as in claim 7 wherein said step of forming a flow reference signal includes the substeps of:

adding said correction signal to the immediately previous flow reference signal to form an intermediate flow reference signal, and limiting the intermediate flow reference signal to a flow reference signal which reflects a change in flow rate through the flow control valve which does not exceed the maximum change in flow rate through the flow control valve that can be obtained within the predetermined short time interval.

9. A method for controlling the flow of a pressurized gas through a flow control valve in a pressurized gas conduit system in response to an electrical pressure input signal indicative of the desired pressure at a specific location in said gas conduit system comprised of the steps of:

generating a delta pressure signal in a feedback loop indicative of the negative of the actual effective pressure at said specific location in the pressurized gas conduit system, adding said delta pressure signal from said pressure input signal to generate a pressure error signal which is indicative of the magnitude and direction of the difference between said pressure input signal and said actual effective pressure, forming a pressure flow correction signal by processing said pressure error signal, forming a flow reference signal by adding said pressure flow correction signal to the immediately previous flow reference signal, generating a control valve position signal from said flow reference signal based on a first predetermined relationship, inputting said control valve position signal to valve control means for varying the effective orifice flow area in said flow control valve in response to a control valve position signal to change the flow rate through said flow control valve, after a predetermined short time interval repeating the steps by first generating a new delta pressure signal and subtracting it from the then current pressure input signal so as to continually correct the flow rate through said flow control valve based on the difference between the measured effective pressure at said specific location and the desired pressure.

10. A method as in claim 9 wherein said step of forming a pressure flow correction signal includes the substeps of:

processing said pressure error signal to form an intermediate pressure flow correction signal, and limiting the intermediate pressure flow correction signal to a pressure flow correction signal whose maximum magnitude reflects a change in flow rate through the flow control valve which does not exceed the maximum change in flow rate through the flow control valve that can be obtained within the predetermined short time interval.

11. A method as in claim 9 wherein said step of forming a pressure flow correction signal includes the substeps of separately processing said pressure error signal and said delta pressure signal and combining the resulting signals to form a pressure flow correction signal.

12. A method for controlling the flow of a pressurized gas through a flow control valve in a pressurized gas conduit system in response to electrical volume and pressure input signals indicative of the desired flow rate and the desired pressure comprised of the steps of:

generating a flow signal in a feedback loop indicative of the actual flow rate of gas flow through said flow control valve, subtracting said flow signal from said volume input signal to generate a correction signal which is indicative of the magnitude and direction of the difference between said flow signal and said volume input signal, forming a volume flow reference signal by adding said correction signal to the immediately previous volume flow reference signal, generating a delta pressure signal in a feedback loop indicative of the negative of the actual effective pressure at a specific location in the pressurized gas conduit system, adding said delta pressure signal from said pressure input signal to generate a pressure error signal which is indicative of the magnitude and direction of the difference between said pressure input signal and said delta pressure signal, forming a pressure flow correction signal by processing said pressure error signal, forming a pressure flow reference signal by adding said pressure flow correction signal to the immediately previous pressure flow reference signal, comparing said pressure flow reference signal to said volume flow reference signal and allowing the larger of the two signals to become the flow reference signal, generating a control valve position signal from said flow reference signal based on a first predetermined relationship, inputting said control valve position signal to valve control means for varying the effective orifice flow area in said flow control valve in response to a control valve position signal to change the flow rate through said flow control valve, after a predetermined short time interval repeating the steps by first generating a new flow signal and subtracting it from the then current input signal so as to continually correct the flow rate through said flow control valve based on the difference between the actual flow rate through the flow control valve and the desired flow rate and the difference between the effective pressure at a predetermined position in the circuit and the desired pressure at that position, whichever demands the higher flow rate.

13. A flow control valve system for use in a pressurized gas system including:

input means for providing a volume input signal indicative of the flow rate desired through a portion of said pressurized gas system, a flow control valve located within said portion of said pressurized gas system, including means for defining a flow control orifice and a movable valve element adapted to be moved so as to change the effective flow control orifice area, valve element drive means for moving said valve element in response to a control valve position signal to said drive means, gas source means for providing a source of pressurized gas to the input of said flow control valve, flow rate means for determining the actual flow rate through said flow control valve and generating a flow signal indicative of said actual flow rate, correction means for taking the difference between said flow signal and said volume input signal to generate a correction signal which is indicative of the magnitude and direction of the difference between said flow signal and said volume input signal, loop means for forming a flow reference signal by adding said correction signal to the immediately previous flow reference signal which has been stored, valve position means for generating a control valve position signal from said flow reference signal based on a first predetermined relationship and inputting said control valve position signal to said valve element drive means.

14. A flow control valve system as in claim 13 wherein said flow rate means includes pressure means for measuring the pressures of the gas upstream and downstream of said flow control valve and generating pressure signals indicative thereof, temperature means for measuring the temperature of the gas flowing through said flow control valve and generating a temperature signal indicative thereof, orifice area means for converting said control valve position signal to a valve orifice signal indicative of the effective orifice area within said flow control valve, and flow processing means for processing said pressure signals, temperature signal and valve orifice signal to form a signal indicative of the actual flow through said flow control valve.

15. A flow control valve system as in claim 14 wherein said orifice area means includes an orifice area look up table derived by empirical testing.

16. A flow control valve system as in claim 15 wherein said orifice area look up table has been derived by empirical testing of the specific flow control valve which is part of the specific system.

17. A flow control valve system as in claim 14 wherein said pressure means includes pressure transducers mounted on a common printed circuit board and conduits connecting said pressure transducers to their respective upstream and downstream positions in the pressurized gas system.

18. A flow control valve system as in claim 13 wherein said valve position means includes:

position conversion means for converting the flow reference signal to a valve reference signal in accordance with a first predetermined relationship, position error means for comparing said valve reference signal to the current control valve position signal to form a valve position error signal position limiting means for limiting the maximum magnitude of the valve position error signal to a predetermined maximum value, which value is based on the maximum correction to the change in orifice area that can be obtained within the time interval used in the sampling/correction, and adding means for adding said limited valve position error signal to the control valve position signal to form a new control valve position signal.

19. A flow control valve system for use in a pressurized gas system including:

input means for providing a volume input signal indicative of the flow rate desired through a portion of said pressurized gas system, a flow control valve located within said portion of said pressurized gas system, including means for defining a flow control orifice and a movable valve element adapted to be moved so as to change the effective flow control orifice area, valve element drive means for moving said valve element in response to a control valve position signal to said drive means, gas source means for providing a source of pressurized gas to the input of said flow control valve, flow rate means for determining the actual flow rate through said flow control valve and generating a flow signal indicative of said actual flow rate, said flow rate means including pressure means for measuring the pressures of the gas upstream and downstream of said flow control valve and generating pressure signals indicative thereof, temperature means for measuring the temperature of the gas flowing through said flow control valve and generating a temperature signal indicative thereof, orifice area means for converting said control valve position signal to a valve orifice signal indicative of the effective orifice area within said flow control valve, and flow processing means for processing said pressure signals, temperature signal and valve orifice signal to form a signal indicative of the actual flow through said flow control valve, correction means for taking the difference between said flow signal and said volume input signal to generate a correction signal which is indicative of the magnitude and direction of the difference between said flow signal and said volume input signal, loop means for forming a flow reference signal by adding said correction signal to the immediately previous flow reference signal which has been stored, valve position means for generating a control valve position signal from said flow reference signal and inputting said control valve position signal to said valve element drive means.

20. A flow control valve system as in claim 19 wherein said loop means includes:

means for forming an intermediate flow reference signal by adding said correction signal to the immediately previous flow reference signal, and flow limiting means for limiting said intermediate flow reference signal to a flow reference signal which reflects a change in flow rate through said flow control valve which does not exceed the maximum change in flow rate through said flow control valve that can be obtained within a predetermined short time interval.

21. A flow control valve system for use in a pressurized gas system including:

input means for providing a pressure input signal indicative of a desired effective pressure at a specific location in said gas system, a flow control valve located within said portion of said pressurized gas system, including means for defining a flow control orifice and a movable valve element adapted to be moved so as to change the effective flow control orifice area, valve element drive means for moving said valve element in response to a control valve position signal to said drive means, gas source means for providing a source of pressurized gas to the input of said flow control valve, delta pressure means for generating a delta pressure signal in a feedback loop indicative of negative of the actual effective pressure at said specific location in the gas system, pressure correction means for comparing said delta pressure signal with said pressure input signal to generate a pressure error signal, pressure processing means for forming a pressure flow correction signal by processing said pressure error signal, pressure reference means for forming a flow reference signal by adding said pressure flow correction signal to the immediately previous flow reference signal which has been stored, and valve position means for generating a control valve position signal from said flow reference signal based on a first predetermined relationship and inputting said control valve position signal to said valve element drive means.

22. A flow control valve system for use in a pressurized gas system including:

first input means for providing a pressure input signal indicative of a desired effective pressure at a specific location in said gas system, a flow control valve located within said portion of said pressurized gas system, including means for defining a flow control orifice and a movable valve element adapted to be moved so as to change the effective flow control orifice area, valve element drive means for moving said valve element in response to a control valve position signal to said drive means, gas source means for providing a source of pressurized gas to the input of said flow control valve, delta pressure means for generating a delta pressure signal in a feedback loop indicative of the negative of the actual effective pressure at said specific location in the gas system, pressure correction means for comparing said delta pressure signal with said pressure input signal to generate a pressure error signal, pressure processing means for forming a pressure flow correction signal by processing said pressure error signal, pressure reference means for forming a pressure flow reference signal by adding said pressure flow correction signal to the immediately previous pressure flow reference signal which has been stored, second input means for providing a volume input signal indicative of the flow rate desired through a portion of said pressurized gas system, flow rate means for determining the actual flow rate through said flow control valve and generating a flow signal indicative of said actual flow rate, correction means for comparing said flow signal with said volume input signal to generate a correction signal which is indicative of the magnitude and direction of the difference between said flow signal and said volume input signal, loop means for forming a volume flow reference signal by adding said correction signal to the immediately previous volume flow reference signal which has been stored, pressure augmentation means for comparing said volume flow reference signal to said pressure flow reference signal and allowing the larger of the two signals to become the flow reference signal, valve position means for generating a control valve position signal from said flow reference signal based on a first predetermined relationship and inputting said control valve position signal to said valve element drive means, and valve position means for generating a control valve position signal from said flow reference signal based on a first predetermined relationship and inputting said control valve position signal to said valve element drive means.

* * * * *